United States Patent [19]
Williams, Jr.

[11] Patent Number: 5,783,146
[45] Date of Patent: *Jul. 21, 1998

[54] SPORICIDAL COMPOSITIONS, STERILIZATION DEVICES AND METHODS FOR RAPID CLEANING, DISINFECTION, AND STERILIZATION

[76] Inventor: Robert M. Williams, Jr., 4568 Argyle Ter., NW., Washington, D.C. 20011

[*] Notice: The term of this patent shall not extend beyond the expiration date of Pat. No. 5,447,684.

[21] Appl. No.: 708,604

[22] Filed: Sep. 5, 1996

Related U.S. Application Data

[63] Continuation-in-part of Ser. No. 162,312, Dec. 6, 1993, Pat. No. 5,447,684, which is a continuation-in-part of Ser. No. 991,093, Dec. 15, 1992, abandoned.

[51] Int. Cl.⁶ ............................................. A61L 2/16
[52] U.S. Cl. ..................... 422/26; 422/36; 422/292; 422/300
[58] Field of Search ................... 422/20, 36, 292, 422/300

[56] References Cited

U.S. PATENT DOCUMENTS

| | | |
|---|---|---|
| 1,817,530 | 7/1931 | Spanel . |
| 3,282,775 | 11/1966 | Stonehill . |
| 3,652,420 | 3/1972 | Hill ........................................ 510/116 |
| 3,708,263 | 1/1973 | Boucher . |
| 3,811,830 | 5/1974 | DeMarco . |
| 3,852,075 | 12/1974 | Basadur . |
| 3,881,940 | 5/1975 | Amundsen et al. . |
| 3,912,450 | 10/1975 | Boucher . |
| 4,093,744 | 6/1978 | Winicov et al. . |
| 4,224,367 | 9/1980 | Scholle . |
| 4,362,241 | 12/1982 | Williams . |
| 4,431,631 | 2/1984 | Clipper et al. . |
| 4,446,967 | 5/1984 | Halkyard . |
| 4,537,778 | 8/1985 | Clipper et al. . |
| 4,593,046 | 6/1986 | Gruber ........................................ 514/717 |
| 4,863,480 | 9/1989 | Buguat et al. ............................... 8/408 |
| 4,941,989 | 7/1990 | Kramer et al. . |
| 4,985,425 | 1/1991 | Chiba et al. ................................ 514/222.2 |
| 5,019,346 | 5/1991 | Richter et al. . |
| 5,038,963 | 8/1991 | Pettengill et al. . |
| 5,084,210 | 1/1992 | Teeters ........................................ 252/392 |
| 5,118,444 | 6/1992 | Nguyen . |
| 5,208,257 | 5/1993 | Kabara . |
| 5,234,719 | 8/1993 | Richter et al. . |
| 5,317,003 | 5/1994 | Kassebaum et al. . |
| 5,393,330 | 2/1995 | Chen et al. . |
| 5,447,684 | 9/1995 | Williams ........................................ 422/20 |
| 5,518,993 | 5/1996 | Lee et al. . |
| 5,540,934 | 7/1996 | Touitou ........................................ 424/450 |
| 5,543,085 | 8/1996 | Miner ........................................ 510/118 |
| 5,656,572 | 8/1997 | Kuchikata et al. . |

*Primary Examiner*—Timothy McMahon
*Attorney, Agent, or Firm*—Beveridge, DeGrandi, Weilacher, & Young, LLP

[57] ABSTRACT

Compositions, devices, and methods are disclosed for achieving rapid cleaning, disinfection, and sterilization in aqueous solution. A device for reducing surface tension in liquids is also disclosed. An ethoxylated aliphatic amine is disclosed as the cationic surfactant of choice, preferably with a liquid soluble germicide simultaneously present in aqueous solution to accelerate sterilization at 25° room temperature. One device includes a tablet; another device includes an absorbent body, or other carriers which can carry both cationic surfactants and germicides. Another device includes an hermetically sealable envelope, which contains both the cationic surfactant and a germicide which impregnates an absorbent liner. The composition includes a germicide and a cationic surfactant. Glutaraldehyde is the preferred germicide, while bis (2-hydroxyethyl) cocoamine and polyoxyethylene (5) cocoamine are, respectively, the cationic surfactant of choice. The compositions can additionally include a nonionic surfactant. A sterilization method is performed by providing a chamber which is substantially impervious to gas and liquid, placing a contaminated object in the chamber, removing air from said chamber and, after air is removed, introducing a sporicidal composition into the chamber to achieve sterilization thereof.

29 Claims, 2 Drawing Sheets

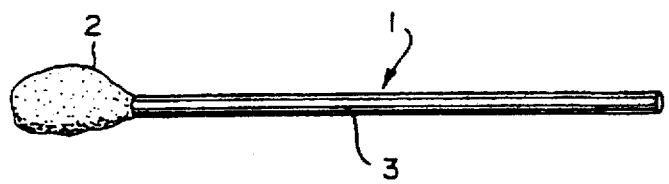
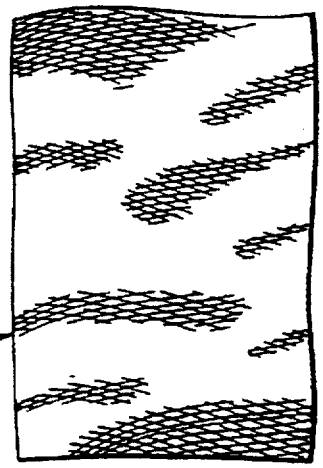
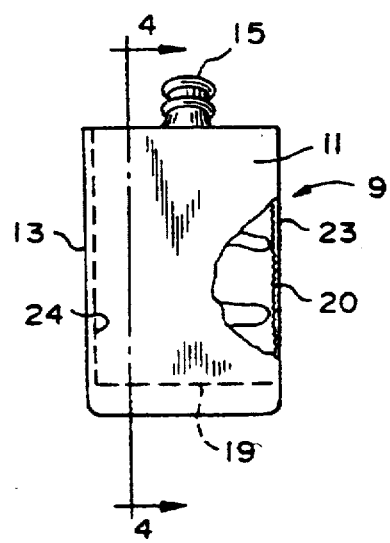
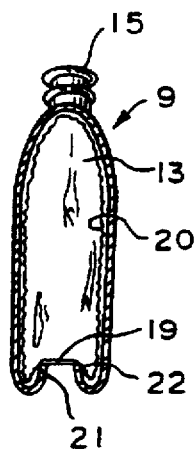
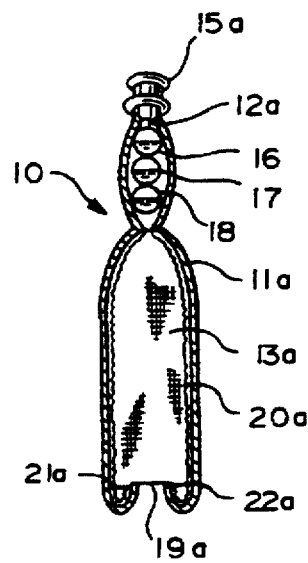

SPORICIDAL COMPOSITIONS, STERILIZATION DEVICES AND METHODS FOR RAPID CLEANING, DISINFECTION, AND STERILIZATION

REFERENCE TO RELATED APPLICATIONS

This is a continuation-in-part of my U.S. patent application Ser. No. 08/162,312 filed Dec. 6, 1993, now U.S. Pat. No. 5,447,684, which was a continuation-in-part of U.S. patent application 07/991,093, filed Dec. 15, 1992, now abandoned. These prior applications are incorporated herein by reference.

BACKGROUND OF THE INVENTION

Autoclaving, dry heat and chemical vapor sterilization methods have been accepted as most effective means for sterilizing inanimate objects such as medical and dental instruments and equipment used in patient treatment. Such methods, however, do have certain disadvantages. The processes are too tedious and cumbersome, and they require long contact times to achieve sterilization. Further, the sterilization process requires highly skilled personnel to operate and monitor the system. Many pieces of equipment, surgical instruments and material used in patient treatment are heat sensitive and too delicate to be exposed to sterilization methods requiring high temperatures. Additionally, some objects which require sterilization are not convenient to sites where the sterilization procedures are performed.

There has been a considerable amount of research directed to finding alternative methods for sterilizing other than those procedures requiring high temperatures. Many of the research efforts have pointed to sterilizing in liquid phase. A search of the scientific literature and the prior art has produced many examples directed to improving the aqueous sporicidal composition of germicides used to disinfect animate and inanimate surfaces and objects.

Glutaraldehyde in aqueous solution has received considerable attention aimed at increasing its potency and rapidity of sporicidal activity by the use of various combinations of active ingredients; or by increasing the temperature of the aqueous solution of glutaraldehyde enhanced by ultrasonic energy. Chemical vapor sterilization has made great strides in enhancing rapid sterilization. This is particularly true of the Steris Company® machine which employs peracetic acid as a chemical vapor generating substance, while the latter can sterilize within 30 minutes, its cost is extremely high. This is also true of the Johnson & Johnson, Inc. hydrogen peroxide sterilization device. It achieves rapid sterilization, but requires a very high capital outlay for the said sterilizer. The use of various surface active agents such as surfactants have been employed to increase the antimicrobial efficacy of aqueous solution of germicides. To date, however, aqueous solutions of glutaraldehyde require from 10 hours to 12 hours contact time to destroy highly resistant spores such as *Bacillus subtilis* and *Clostridium sporogenes*. For this reason, aqueous solutions of glutaraldehyde are still relegated to a high level disinfecting role.

Various liquid germicides hold out great promise as liquid sterilants if their antimicrobial properties can be accelerated to considerably shorten the contact time needed for sporicidal kill. The need for germicides in liquid phase having rapid and potent disinfecting and sterilizing compositions is highly desirable for inactivating microorganisms on inanimate and animate surfaces and objects. Germicides employed to disinfect and sterilize inanimate objects are termed "disinfectants"; those germicides employed to disinfect and sterilize animate surfaces are termed "antiseptics." This invention's efficacy is directed to the enhancement of aqueous germicidal solutions used as disinfectants and antiseptics in the treatment of both inanimate and animate surfaces and objects. Germicides should be able to penetrate into crevices, cavities, and beneath films of organic matter. Moreover, germicides should possess and maintain a strong lethal concentration in the presence of sputum, blood and fecal material. Germicides should have a wide antimicrobial spectrum; and importantly, germicides should achieve and maintain a low surface tension to enable effective and rapid absorption of the active ingredients at interface with a contaminated object. The sporicidal composition should be able to rapidly permeate, flood, and kill the microorganisms intercellular mass.

The present invention is able to address many of the objectives discussed above. The sporicidal composition of the present invention is able to rapidly kill highly resistant spores within 5–90 minutes. When the present sporicidal composition is employed in an aqueous solution of glutaraldehyde, sterilization is achieved within 90 minutes. When the same composition is used within an envelope which is substantially liquid and gas impervious, sterilization is achieved within 30 minutes; and when the above procedure is repeated employing vacuum, highly resistant spores such as *Clostridium sporogenes* and *Bacillus subtilis* are inactivated within 5 minutes. The present composition, when placed in a sterilization device that is substantially impervious to liquids and gases, the sterilization procedure is dramatically enhanced by the use of vacuum and the synergistical effects obtained by the trapping of germicidal vapors. The present invention can be practiced without expensive capital sterilization equipment, is extremely easy for health personnel to use, and is most effective and reliable as will be revealed later in this document. The efficacy of the present invention is directed to a potent sporicidal composition observed when certain aliphatic cocoamines (cationic surfactants) are combined with specific germicidal agents, preferably an aqueous glutaraldehyde. The resulting sporicidal composition is able to rapidly reduce the contact time needed for sporicidal kill from hours to minutes, and from minutes to seconds. This invention's sporicidal efficacy is dramatically enhanced when certain specific cationic surfactants are employed in a germicidal aqueous solution. While there is an extensive and broad array of cationic surface active surfactants termed ethoxylated aliphatic amines, the inventor has discovered that only a very limited choice is available for use in the present composition.

The surfactants of choice selected from this class for use in the present composition are ethoxylated aliphatic amines having from 2–30 moles of ethylene, and are generally represented by the formula listed below.

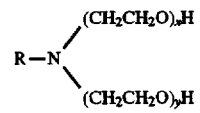

The specific aliphatic amine cationic surfactants of choice for use in the present invention are listed below with their chemical names and their trade names:

| Chemical Name | Trade Name | TSCA No. |
|---|---|---|
| *Bis (2-hydroxyethyl) cocoamine Ethoxylated (2) cocoakylamine | Ethomeen $C_{12}$ | 61791-31-8 |
| *Polyoxyethylene (5) cocoamine Ethoxylated (5) cocoakylamine | Ethomeen $C_{15}$ | 61791-14-8 |
| *Polyoxyethylene (10) cocoamine Ethoxylated (10) cocoakylamine | Ethomeen $C_{20}$ | 61791-14-8 |
| *Polyoxyethylene (15) cocoamine Ethoxylated (15) cocoakylamine | Ethomeen $C_{25}$ | 61791-14-8 |
| *Polyoxyethylene aliphatic amine Ethoxylated (20) cocoakylamine | Ethomeen $C_{12/12}$ | |

*Alternative Chemical Name

The above chemicals are produced by the Akzo Nobel Chemie Americo Organic Chemicals (300 S. Riverside Plaza, Chicago, Ill. 60606).

While the present invention benefits well by the use of all of the above ethoxylated aliphatic amines, the preferred ones are Bis (2-hydroxyethyl) cocoamine, and polyoxyethylene (5) cocoamine, or a mixture of the two. The amount of the above cationic surfactants recommended for use in the present composition vary from 0.001 to 2.0% by weight.

When an aqueous solution containing the disclosed cationic surfactant and an antimicrobial agent (i.e., glutaraldehyde), the contact time required for total sporicidal kill is reduced from 10–12 hours to 60–90 minutes. Povidone-iodine requires 53 hours to become sporicidal. When enhanced with the disclosed cationic surfactant that contact time is reduced to 2.5 hours. The same accelerated kill is observed on susceptible microorganisms when employing germicides such as alcohol compounds, chlorine compounds, quaternary ammonium salts, iodophors and other like compounds. This rapid antimicrobial activity is unaffected by ph. Aqueous microbial solutions having cleaning, disinfecting, antiseptic, or sterilizing composition are dramatically enhanced in cleaning ability and in reducing the contact time required for total antimicrobial inactivation. Without altering the composition of an existing aqueous antimicrobial solution, the composition of the present invention can be added directly to said existing composition with dramatic results in reducing antimicrobial contact time. Where incompatibility exists between components in the present composition and those components in existing compounds, reformulation of the existing product may be necessary. This is particularly significant when adding the present composition to one having an anionic surfactant in its composition (Cidex® glutaraldehyde); on the other hand when the present composition is added to one having a nonionic, cationic or amphoteric surfactant (Banicide® glutaraldehyde) rapid accelerated antimicrobial kill is achieved. When the present cationic surfactant is employed in an aqueous germicidal solution, the need for long contact time for maximum germicidal activity is eliminated.

The role of aqueous glutaraldehyde can be elevated from a high disinfecting role to that of a rapid liquid sterilant. A germicide used as an antiseptic and supplemented with this cationic surfactant is able to rapidly reduce the microorganism population residing on animate surfaces such as skin, mucosal membrane and wound sites; it can be used to treat the oral mucosa and its related structures. The application of the present invention is not limited to cleaning, disinfecting, and sterilizing proposed for use in the health field. It can be used to enhance the antimicrobial activity of aqueous solutions and gels employed as mouth rinses, toothpaste, soaps, detergents and many other similar products intended to remove foreign material including microorganisms from animate and inanimate surfaces and objects. When the present sporicidal composition is employed in an aqueous solution, sterilization is achieved within 60–90 minutes. It should be noted, however, that the present composition can not enhance the sporicidal activity of a non-sporicidal germicide. It can only accelerate contact time needed to inactivate microorganisms.

As previously stated, chemical vapor sterilization is an effective and acceptable method of destroying all forms of microorganisms. The use of vapor generating chemical substances whose emitted vapors are lethal to microorganisms include hydrogen peroxide, peracetic acid, and ethylene oxide. While extremely effective, however, chemical vapor sterilization procedures have many disadvantages: the cost for capital equipment needed is extremely expensive; highly trained and skilled personnel are needed to operate, monitor, and maintain the system; and special precautions are necessary to protect health personnel and others from the harmful vapors generated by the system. The present invention is able to eliminate the above objections to the use of chemical vapor sterilization. It requires no expensive equipment necessary to perform the sterilization procedure; health personnel and the lay population will find the system simple to operate and monitor; the present invention can be made available to sites and areas where sterilization procedures are not now available; the sterilization procedure is extremely rapid and effective; and the components employed in the practice of the sterilization system are disposable.

The present invention includes a sterilization device comprising a liquid-gas impervious envelope having an inner absorbent material or lined chamber. The latter has a hermetically sealable opening into said chamber. Additionally the envelope has a means for achieving subatmospheric pressure within the inner chamber. When the present sporicidal composition and a contaminated object are introduced into the inner chamber and the opening is hermetically sealed, sterilization is achieved within 30 minutes. It should be noted that only sufficient composition is added to saturate the absorbent liner.

When the above procedure is repeated and vacuum is applied to the system, sterilization is achieved within 5–10 minutes. When an unsupplemented glutaraldehyde replaces the sporicidal composition, and the above procedure is repeated, sterilization is achieved within 30 minutes. By the use of vacuum alone within this sterilization device, sterilization is achieved with unsupplemented glutaraldehyde, which requires 10–12 hours to achieve sterilization in the regular AOAC immersion system.

The dramatic and pleasing results achieved within this sterilization device is due to the synergistic use of liquid and vapors and vacuum.

It is accordingly one object of the present invention to present potent sporicidal composition which can rapidly destroy highly resistant spores within minutes when practiced within the scope of the invention. It is a further object of this invention to demonstrate the powerful enhancement and acceleration of the antimicrobial activity of various germicides when exposed to the disclosed composition in various aqueous solutions. In addition to the powerful sporicidal composition enhanced with specific cationic surfactant, it is another object of the present invention, when employing the present composition, to disclose a device for further sporicidal accelerated enhancement by the use of vacuum and by trapping the germicidal gases and vapor pressure generated within said device. And, finally, it is another object to demonstrate the many applications where the present composition and devices can be applied within the scope of the invention.

Referring now to the novelty and the innovativeness of the present invention, a search of the scientific literature and the prior art reveal no instance where cationic surfactants selected from that class of surface active agents termed ethoxylated aliphatic amines have ever been used as surface active agents in disinfectants or antiseptic germicidal solutions including aqueous glutaraldehydes. For example, U.S. Pat. No. 3,252,775 (Stonehill) discloses a very extensive list of chemical agents that could have been used in his issued U.S. Patent. While the inventor lists a wide variety of surface active agents derived from fatty amines, fatty amides, quaternary ammonium salts, etc., he makes no attempt to select nor describe a specific agent(s) for use in said patent. To the contrary, the inventor selects for use in his patent cetylpyridinium chloride, a quaternary ammonium salt which he had not previously described nor disclosed except in his claims. For reference, enclosed is the inventor's (Stonehill) discussion of agents that could be used in his issued U.S. patent. Nowhere in his disclosure is there a reference to the ethoxylated aliphatic cocoamines claimed for use in the composition of the present invention. Below is a direct quote from Stonehill's U.S. Pat. No. 3,252,775 relative to his (Stonehill) selection of a cationic surfactant.

The cationic surface active agents which may be used in the novel compositions of the present invention are the aliphatic or fatty amines and their derivatives such as dodecylamine, hexadecylamine, hexadecylamine hydrochloride; homologs of aromatic amines having fatty chains such as dodecyl aniline; fatty amines derived from aliphatic diamines or disubstituted diamines such as oleylaminodiethylamine; amides obtained from amino alcohols and their quaternary ammonium derivatives such as the fatty acid hydroxyethyl amides; quaternary ammonium bases derived from the fatty amides of disubstituted diamines such as oleyl methylamino ethylene diethylamine methyl sulfate, oleyl benzylamino ethylene diethyamine hydrochloride; fatty amides derived from benzimidazolines such as the alkylated benzimidazolines made by the condensation of fatty acids with aliphatic diamines; basic pyridinium compounds and their salts such as the sulfate of lauryl pyridinium, octadecyl methylene pyridinium acetate; basic sulfonium, phosphonium and antimonium compounds such as the methyl sulfate of dimethyloctadecyl sulfonium; betaine compounds of quaternary ammonium such as betaine compound of diethyl aminoacetic acid and octadecyl chloromethyl ether; the urethanes or basic salts of ethylene diamine such as the hydrochloride of menthol diurethane; polyethylene diamines and their quaternary ammonium derivatives; polypropanol polyethanolamines; and preferably the quaternary ammonium salts having a hydrophobic group such as cetyltrimethyl ammonium chloride, alkyldimethyl benzyl ammonium chloride, diisobutyl phenoxyethoxy ethyldimethyl benzyl ammonium chloride, dimethylstearyl hydroxyethyl ammonium chloride, oleylmethyl aminoethylene diethylamine methyl sulfate, the chloride of the methyl ester of dimethyloctadecyl betaine, dimethylphenylbennzyl ammonium chloride, and the like.

The germicide for use in the present composition can be selected from a broad and extensive array of antimicrobial agents. They include iodophors, chlorine compounds, alcohol compounds, quaternary ammonium salts, sodium perborate, phenolic compounds, antiseptic, tricloson, antiplaque agents, topically applied antibiotics, hydrogen peroxide, glutaraldehyde, and other chemical agents capable of generating vapors lethal to microorganisms. The germicide of choice, however, for use in the present composition is glutaraldehyde which comprises 0.01–2.5% by weight of the aqueous germicidal solution. The said glutaraldehyde comprises a saturated dialdehyde having from 2 to 6 carbon atoms. Another solution can have a sufficient quantity of a lower alkanol to make a final alcohol concentration from about 60 to about 70% by weight. A glutaraldehyde composition can include an alkaline salt providing the solution with a ph of about 7–8. Other glutaraldehyde solutions may have a ph of from 1 to 7. The surfactant employed in the glutaraldehyde solution is a cationic surfactant. Such solutions may also contain a nonionic surfactant; the preferred ionic surfactant is ethoylate of linear alcohol.

SUMMARY OF THE INVENTION

The present invention relates to a rapid sporicidal composition which includes a cationic surfactant and a liquid soluble germicide. The cationic surfactant is preferably one selected from the class ethoxylated aliphatic cocoamines, or a mixture thereof. The liquid soluble germicides are selected from the class or groups including quaternary ammonium salts, chlorine compounds, alcohol compounds, iodophors and antiseptics applied to animate surfaces, antibiotics, and glutaraldehydes. Aqueous glutaraldehyde is preferred for the rapid cleaning, disinfecting, and sterilization of inanimate objects and surfaces. Povidone-iodine is the germicide of choice for the treatment of animate surfaces.

In another respect the present invention relates to a device for enhancing and accelerating the antimicrobial activity of a liquid soluble germicide. The device comprises a cationic surfactant, and/or a germicide incorporated into a tablet, a powder, a porous substance, or on a suitable substrate. When the specific surfactant selected for use in the present invention is mixed with an existing aqueous germicide solution, the latter's antimicrobial activity is instantly enhanced and accelerated. When the cationic surfactant and germicide are added and mixed in an aqueous solution, a potent and rapid germicidal solution is achieved.

The present invention also relates to a sterilization device which includes an envelope which is substantially impervious to both a gas and liquid. The envelope contains an inner chamber which is hermetically sealable. The entry into the inner chamber permits the entry of an object into said inner chamber. The inner chamber is preferably lined with a nonwoven absorbent material. This sterilization device is provided with means for achieving vacuum in the inner chamber. The latter, when in use, contains a germicidal solution. Both the cationic surfactant and a suitable germicide may be constituents of the absorbent liner in a nonreactive state until exposed to a liquid. In lieu of having constituents of the absorbent liner, the cationic surfactant and the liquid soluble germicide can be contained in a crushable capsule(s).

A nonwoven fabric is broadly defined as sheet or web structures made by bonding or entangling fibers or filaments by chemical, thermal or mechanical means. They are not made by the traditional processes of weaving or knitting. Generally, nonwoven fabrics contain three systems in their manufacturing processes. These include a fiber system, binder system and finish system. The fiber system refers to the fibers used in the nonwoven. The binder system refers to the means of bonding the fiber together in a web-like structure. The finish system refers to the properties imparted to the nonwoven such as appearance, durability, strength, softness—and importantly—wickering and wetting properties.

Important to accomplishing these manufacturing systems in nonwoven production calls for the use of an array of chemical compounds. The chemical compounds include, but are not limited to, polymer types such as acrylics, styrene-butadene, vinylacetate acrylics, urea and melamine formaldehyde. Chemicals used in the finishes are formulated from mixtures of lubricants, antistatic agents and compounds chosen from those used as surfactants. The nonwoven fabric of choice for use in this invention is one that has the following specifications:

Binder Type: Acrylic

Fiber Content: 100% Rayon

Grade Number: 2007022

Weight: 0.7 oz/yd

Furnish: Rayon

Manufacturer: International Paper Company 77 West 45th Street New York, N.Y. 10036

And finally, the present invention relates to a rapid germicidal composition comprising a cationic surfactant and a liquid soluble germicide that can be used to enhance and accelerate the antimicrobial activity of dentifrices, mouth rinses, soaps, detergents and many industrial and household aqueous germicidal products. It can be incorporated into wipes and surgical sponges.

BRIEF DESCRIPTION OF THE DRAWINGS

FIG. 1 is a side view of a swab applicator in accordance with the present invention.

FIG. 2 is an elevational view of flat liquid absorbent fabric in accordance with the present invention.

FIG. 3 is an elevational view of an envelope and related components in accordance with the present invention.

FIG. 4 is a cross-sectional view taken on the line 4—4 of FIG. 3.

FIG. 5 is a cross-sectional view of an envelope of a further embodiment of the invention.

DESCRIPTION OF THE PREFERRED EMBODIMENTS

Figure 6:
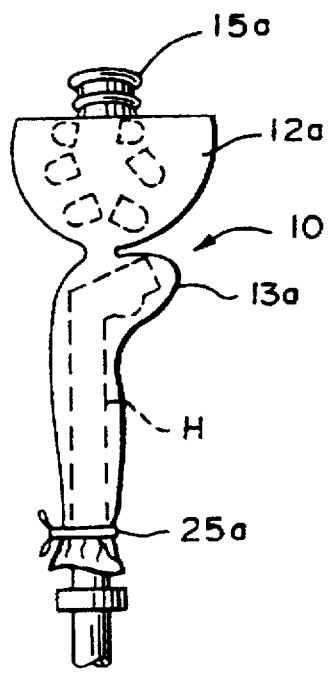
FIG. 6 is a side view of another embodiment of the present invention with an instrument in place.

Referring now to the drawings, wherein like or corresponding reference numerals are used to designate like or corresponding parts throughout the several views, there is shown in FIG. 1 a device 2 resembling a swab applicator. The device 2 comprises a liquid absorbent member which is attached to handle 3. The absorbent member 2 is preferably a nonwoven fabric containing as constituents the rapid sporicidal composition of claim 1 previously milled into said liquid absorbent member 2 at the manufacturing stage; or the sporicidal composition can be disposed in a dry state in the absorbent fabric so that said composition is in a nonreactive state until the said fabric is exposed to a liquid whereby the rapid sporicidal composition is activated. The liquid absorbent member 2 can additionally contain other active ingredients such as iodophors, including povidone-iodine, various quaternary salts, and the like.

FIG. 2 shows a device 5 which is a flat porous liquid absorbent fabric containing the rapid sporicidal composition or the germicide and cationic surfactant which occupy different areas of the fabric in a dry and non reactive state.

In use, when either of the devices 1 and 5, previously dosed with the rapid composition, is saturated with an aqueous solution, the antimicrobial properties of the solution are considerably accelerated and enhanced. When the devices 1 and 5 of FIGS. 1 and 2 are exposed to an aqueous solution having cleaning, disinfecting and sterilizing properties their antimicrobial properties are dramatically and significantly enhanced. The significance of the surface active activity achieved by germicide and cationic surfactant in aqueous solution makes this invention extremely useful for enhancing aqueous solutions of antiseptics employed for decontaminating animate surfaces and objects. This invention, moreover, can be extremely useful in enhancing antiseptics used for application to wound sites and topical applied medicaments to skin and mucosal tissue. Other uses of this invention include their employment in mouth washes, toothpaste, and other household products having an aqueous medium such as soaps and detergents. Device 5 of FIG. 2, when employing glutaraldehyde as the preferred germicide in the rapid sporicidal composition, would be ideal in wiping and decontaminating environmental surfaces and objects in the health field areas and in the home and industry.

As previously stated, a preferred cationic surfactant is bis (2 hydroxyethyl) cocoamine or a quaternary ammonium salt, which constitutes about 0.01 to 2% by weight of the sporicidal composition. The invention may also be practiced with other germicides such as quaternary ammonium compounds, phenols, iodophors, chlorine compounds, alcohol compounds, and hydrogen peroxide.

In addition to the absorbent fabric of devices 1 and 5 of FIGS. 1 and 2, carriers for the constituents in a dry form may be powders, tablets, porous members, woven and nonwoven fabrics, nonporous substrates, and plastics such as polyethylene into which the surfactants and other constituents have been milled. The cationic and germicide constituents are in a nonreactive state when they occupy different areas of the carrier. Various carriers such as water and alcohol may be used when the constituents are in solution.

Additional uses of devices 1 and 5 of FIGS. 1 and 2 are in the health field where they provide the sporicidal composition in sponges, dressings, wipes, bandages, and incontinence products, to mention a few.

The sporicidal composition can be used in an aerosol spray for surface and space disinfection.

There is shown in FIG. 3 a device 9 which includes an envelope 11 which comprises a flaccid, liquid/gas impervious material, thereby preventing the escape of liquids and gases from said device. The material of said device is deformable or crushable about an instrument or object which is placed within it, so as to conform substantially to the external shape of the object. A suitable material for envelope 11 is polyethylene, which is heat sealable. Another suitable material is a lamination of flexible sheet material. Within chamber 13 is an absorbent liner 20, which preferably is a nonwoven fabric. The liner 20 is bonded to envelope 11 on its interior walls at 21 and 22 spaced inwardly of and near the opening 19. The liner material 20 contains, as constituents, cationic surfactants which have been milled into said liner at the manufacturing stage. The opening 19 is sealable with a tie cord, heat seal, adhesive flap, or by other suitable means. There is positioned at the closed end of envelope 11 a valve 15 which is connectable to a vacuum source to achieve vacuum in chamber 13.

Referring now to FIG. 4, a view taken on 4—4 FIG. 3, there is shown device 9 with opening 14a which is a gap in the heat seal line 14, providing communication between chamber 13 and valve 15. This makes it possible to achieve vacuum and to introduce fluids into the vacuumized chamber 13 by way of valve 15.

In use, an object having irregular surfaces and internal recesses and cavities, such as a medical endoscopes and a dental handpiece, is placed into chamber 13 through opening 19. The opening 19 is sealed hermetically. A vacuum is drawn through valve 15, thereby creating subatmospheric pressure in chamber 13. The present germicidal composition, preferably a glutaraldehyde, is introduced into chamber 13 through valve 15 in a quantity sufficient to permeate and to saturate liner 20. The saturated liner 20 clings and conforms to the exterior shape of the object contained therein. Any surfactant or germicide contained as dry constituents within said liner 20 is released to interact and become activated when exposed to a liquid, thereby causing dramatic and significant rapid destruction of *Clostridium sporogenes* and *Bacillus subtilis* inoculated on suture loops within 5–10 minutes at 25° C. when accompanied with vacuum. The sterilization process is further enhanced by subjecting it to ultrasonic waves if desired. The use of vacuum is extremely important in this device to assure that the sporicidal liquid is exposed to all surfaces of the object contained in chamber 13. When the contaminated object is devoid of irregular and internal surfaces, the use of vacuum may not be needed. The significance of this system is the discovery of the potent surface active properties of an aliphatic cationic surfactant when employed together in a germicidal aqueous solution; and, moreover, the innovative and unique method of positioning these components in an absorbent material where surfactant, germicide and any vapor emitted by the germicide is in constant contact with the contaminated object.

In use, the device 9 of FIGS. 3 and 4 requires the following steps:

a contaminated object is placed in chamber 13 through opening 19;

the opening 19 is sealed;

a vacuum is drawn in chamber 13 through valve 15;

the disinfecting solution is then introduced into chamber 13 through valve 15;

sufficient contact time is permitted to allow for disinfecting the objects; and the object is removed from chamber 13 through opening 19 and rinsed prior to patient use.

It is important that vacuumizing of the inner chamber precedes the introduction of the sporicidal composition into said inner chamber.

In instances where vacuum is omitted, the contaminated object is placed in chamber 13, the sporicidal composition is introduced through opening 19, and the latter is sealed. Sufficient time is permitted for disinfecting the object. The latter is removed and rinsed prior to patient use.

Referring now to FIG. 5, a device 10 is shown which differs from device 9 in FIG. 3 and FIG. 4 in that there are two chambers, 12a and 13a. Chamber 12a has crushable capsules for containing the cationic surfactants and other enhancers or buffers where desired. The envelope 11 is divided into a first chamber 12a, and a second chamber 13a. The division of the envelope 11 is by a heat seal 14a which extends partially across the width of envelope 11, there being a gap in the heat seal 14a so as to provide communication between the chamber 12a and 13a.

In its first chamber, 12a, there may be seen three (or more if needed) crushable capsules, 16, 17, and 18, which contain germicide and cationic surfactant in separate capsules. Other capsules may contain a buffer or an active ingredient (glutaraldehyde) if so desired; these materials being provided in appropriate quantity relationships in the respective capsules. Within the second chamber 13a is a liner 20a which conforms to the specifications and arrangement of the liner material 20 in device 9 of FIGS. 3 and 4. FIG. 5 reveals a communication between chamber 12a and valve 15a by means of a gap in heat seal 17. In use, the device 10 of FIG. 5 requires the following steps:

the placing of contaminated object into absorbent inner chamber 13a through opening 19a;

the sealing of opening 19a hermetically by suitable means;

drawing vacuum in the two chambers 12a and 13a through valve 15;

crushing the capsules in the unlined chamber 12a;

leaving contaminated object in device 10 for period sufficient for sterilization;

removing object from chamber through opening 19a; and rinsing object prior to patient use.

The embodiments of the invention disclosed in FIGS. 3–5 are extremely effective for cleaning, disinfecting, and sterilizing in liquid/vapor phase a large number of objects which are heat sensitive and for whatever reasons, are unavailable to the traditional methods of disinfecting. This is particularly true of instruments and equipment such as medical endoscopes and dental handpieces having irregular surfaces and internal recesses. Such objects require long contact periods for total destruction in aqueous solution of glutaraldehyde (10–12 hours). In this system, the synergistically effectiveness produced by superior surface active properties, vapors, and vacuum in aqueous solutions of glutaraldehyde destroy *Clostridium sporogenes* and *Bacillus subtilis* within 5–10 minutes.

Referring now to FIG. 6, there is shown the device 10 in use and in position on a dental instrument, specifically a dental handpiece H. The entry provided by the cuffs 21a and 22a and the lower portions of the liner 20a will have been opened and the device 10 moved downwardly over the dental handpiece H. The readily manually crushable capsules 16, 17, and 18 will then have been crushed, the fragments being indicated by the dashed lines in the first chamber 12a in FIG. 3. The crushing of the capsules 16, 17 and 18 has released the cold disinfection solution, its surfactants and its buffer or activator, and the activated solution will have passed from the chamber 12a into the chamber 13a, and permeated the liner 20. The device 10 will then have been sealed and secured about the handpiece H by a tie device 25. Then the device 10 will have been deformed or crushed so as to substantially conform to and engage the entire outer surface of the handpiece H. In this way, the cold disinfection solution is and will remain in contact with substantially the entire outer surface of the handpiece H for the requisite time for this disinfection and for sterilization, where desired.

The dental handpiece H is illustrative of an instrument which is desirably sterilized, but is not amenable to immersion. Other dental or medical instruments may be sterilized within the disclosed devices, as will be readily understood.

Whatever the instrument, and its exterior shape, due to the bonding or adhering of the liner 20a to the envelope 11a in the manner disclosed, the entry of the instrument into the second chamber 13a will not dislodge the liner, and neither will the withdrawal of the instrument from the device 10 dislodge the liner.

Figure 7:
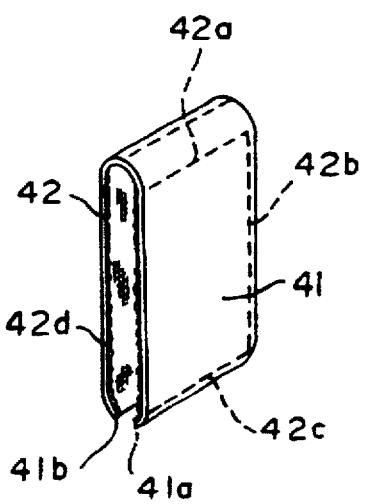
FIG. 7 is a perspective view, partly in cross-section, of a further embodiment of the present invention.

In FIG. 7, there is shown an alternate embodiment, the device 40 shown therein comprising an envelope 41 defining a single chamber without means for achieving vacuum and having therein an absorbent liner 42 which is bonded to the envelope 41 along an upper line 42a, a lateral edge 42b and an edge opposite to the edge 42b which is not shown in FIGS. 3–6. There is also a bonding of the liner 42 along a pair of lower lines 42c and 42d which extend generally parallel to the lower edges 41a and 41b at the lower end of the envelope 41. The lower portions of the two walls of the liner 42 and the lower portions of the walls forming the envelope 41 provide, in registry, an entry into the device 40. The lower edge of the liner 42 does not extend downwardly beyond the lines 42c and 42d, and therefore below these edges there is provided on the envelope 41 a sealing zone at the entry, which may be provided by the material of which envelope 41 is made, or by some additional material applied to the inner lips of the lower portions of the walls of the envelope 41, such material being a releasable sealant, and providing for hermetic sealing of the interior of the envelope 41. In this embodiment, the sporicidal composition solution has been previously provided within the device 40, so as to permeate the liner 42, after which the device 40 is sealed.

In use, the device 40, sealed as indicated and with the absorbent liner 42 permeated with composition solution, is opened at the seal to provide an entry. Objects to be disinfected are inserted within the device 40 or the device 40 is placed over such an object, and is then deformed, as necessary, so that the entire outer surface of the object is engaged by the permeated or saturated liner 42.

Figure 8:
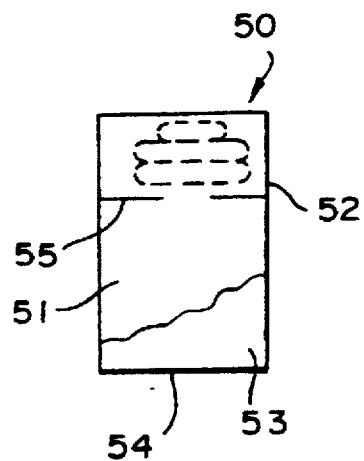
FIG. 8 is a cross-sectional view of another embodiment of the invention.

In FIG. 8, there is shown a device 50 in accordance with the present invention and comprising an envelope 51 of the same material as the envelope 11, being divided into an upper chamber 52 and a lower chamber 53 by a heat seal 55 extending partially across the envelope. Within the first chamber 52 are three capsules 16b, 17b and 18b which contain the same materials, and have the same attributes as the capsules 16, 17 and 18 of the embodiment shown in FIG. 5. In the embodiment of FIG. 7, the second chamber 53 is not provided with a liner, but its lower end has a seal zone indicated generally by the reference numeral 54, provided at the lower ends of the walls forming the second chamber 53, and being positioned so as to seal the entry into the second chamber 53.

In use, an instrument or other object is inserted into the chamber 53, and utilizing the sealing zones 54 and the adhesive qualities thereof, sealing is effected about the instrument or object, or sealing is effected between the two zones 54 if the instrument is of such size as to be completely housed or contained within the chamber 53. Such an instrument may be, for example, a thermometer, a toothbrush or some other instrument which would not be harmed by immersion. Thereafter, the crushable capsules are broke, and the cold disinfection solution is activated and caused to flow into the chamber 53 where it contacts and disinfects the object, or sterilizes the object, if contact occurs for a sufficient length of time.

Figure 9:
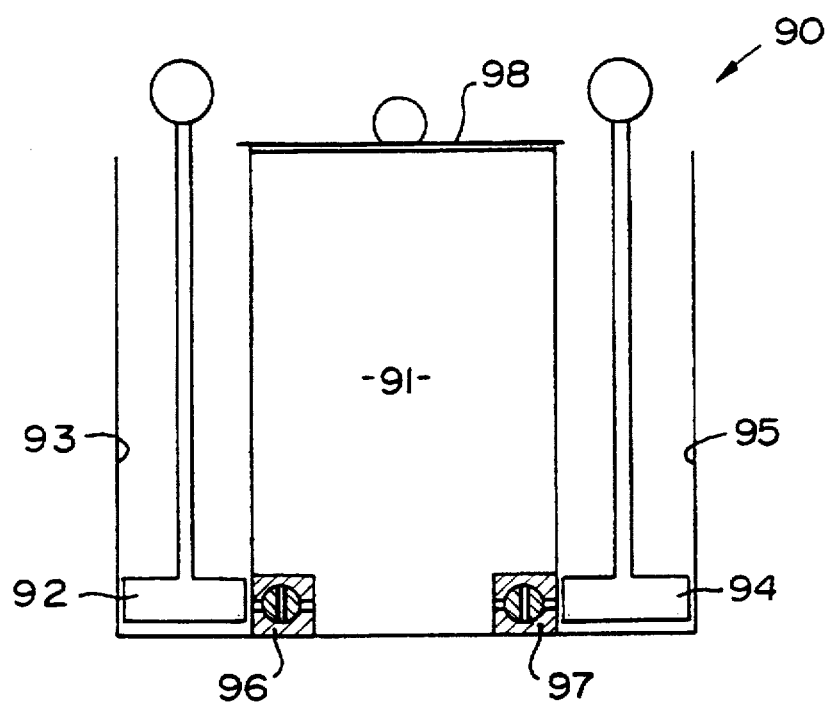
FIG. 9 is a cross-sectional view of an embodiment of a self-contained sterilization device in accordance with the present invention.

FIG. 9 is a diagrammatic view of a preferred embodiment of the present invention in which a device has means for achieving vacuum in the chamber, and means for introducing the sporicidal composition into the chamber.

This device 90 has a treatment chamber 91 for receiving articles to be sterilized, a vacuum pump which includes a piston 92 and a cylinder 93, and a liquid feed pump which includes a piston 94 and a cylinder 95. A vacuum valve 96 connects the vacuum cylinder 93 to the treatment chamber 91. A liquid valve 97 connects the liquid feed cylinder 95 to the chamber 91.

Before contaminated objects are placed in the chamber 91 of device 90, the cylinder 95 is precharged with sporicidal liquid by pouring the liquid into the chamber 91, opening the valve 97, raising the piston 94 to draw liquid into the cylinder 95, and then closing the valve 97.

A contaminated object is first wrapped in an absorbent material and placed in chamber 91, the latter being sealed by a cap 98. Vacuumization of chamber 91 is achieved by opening valve 96 and lifting piston 92 until no more movement is possible. This places the chamber 91 under negative subatmospheric pressure. Valve 96 may then be closed. Valve 97 is then opened effecting communication between cylinder 95 and chamber 91. The piston 94 is depressed and the sporicidal composition from chamber 95 flows into chamber 91 saturating and flooding the absorbent material which covers the contaminated objects. The objects are left for sufficient time for sterilization which is accelerated due to the negative pressure.

In lieu of the surfactants in crushable capsules as shown in device 50 of FIG. 8, or being the constituents of the absorbent material of devices 92a and 100 of FIG. 9, the constituents could be positioned on suitable substrates in the latter devices; or the surfactants could be milled into the polyethylene walls of device 50 of FIG. 8. This is possible according to the current state-of-the-art. The devices 92a and 100 of FIG. 9 could be made from materials such as polystyrene, polystyrofoam, or polyethylene, where the surfactants are contained therein, and or released as indirect additives when exposed to aqueous solutions of various kinds, whereby surface tension is reduced dramatically.

There the absorbent fabric is employed in the various embodiments of the present invention, the said absorbent fabric can be wrapped around an object remote from the sterilization devices, and then inserted into the inner chamber of said sterilization devices.

In review, it is important to note the following advantages the present invention presents over the current state-of-the art:

The present rapid sporicidal composition can achieve sterilization at 25° C. within 60–90 minutes in the regular immersion system 15–30 minutes or less in devices of FIGS. 3, 4, 5, 6, 8, and 9 without vacuum 5–10 minutes in the above device when vacuum is employed 25–30 minutes in the above device employing an unsupple—mented glutaraldehyde, and with vacuum.

EXAMPLES

The following examples illustrate the invention. They are given primarily for the purpose of illustration and should not be construed as limiting the invention to the details given.
Purpose To determine the minimum exposure conditions required for the test system to exhibit sporicidal activity against *Bacillus subtilis* ATCC #19659, and *Clostridium sporogenes* ATCC 3584.
Test Method The test method used was a modification of the sporicidal method, Chapter 4. Disinfectant paragraphs 4.033–4.085, *Official Methods Of Analysis of the Association of Official Analytical Chemists.*

The test germicides used were Ucarcide® reduced to an acid glutaraldehyde, and Banicideo®, a 2% acid glutaraldehyde, and Cidex® (regular), an alkaline glutaraldehyde.

The nonwoven material used was:

Binder Type: Acrylic
Fiber Content: 100% Rayon
Grade Number: 2007022
Weight: 0.7 oz/yd
Furnish: Rayon
Manufacturer: International Paper Company 77 West 45th Street New York, N.Y. 10036

The cationic surfactant used was an ethoxylated aliphatic amine compound.

A modification of the method involved using the pouches as containers for the germicide rather than the 25×150 mm medication tubes specified in the method. The following tests were performed by placing test sutures in pouches of the type shown in FIGS. 3 and 4 wherein the openings 19 were sealed by adhesive tape.

The amount of germicide used in each pouch was 12 ml. All tests were conducted at 25° C.

All cultures in pouches were incubated for 21 days after which they were heat shocked.

An illustration of the pouch employed in testing the efficacy of the invention is presented below:

Example I

Forty (40) nylon sutures were contaminated with a 72-hour culture of Clostridium sporogenes ATCC #3584. The suture loops were exposed to a 2% acid glutaraldehyde solution (Banicide®) supplemented with a cationic surfactant.
Results

| Positive control . . . growth in 24 hours 2/2 | | |
|---|---|---|
| Organism | Carrier | Contact Time |
| Clostridium sporogenes | Sutures | 10 minutes 0/40 |

Discussion

The supplemented 2% acid glutaraldehyde solution proved to be sporicidal within ten (10) minutes when supplemented with anionic and cationic surfactants. These findings are outstanding considering that 6¾ to 10 hours are required to inactivate Clostridium Sporogenes in the conventional immersion system using Banicide®. The acid resistance test was 10 minutes.

Example II

Because of the outstanding results obtained in Example I, the test was repeated reducing the contact time to five (5) minutes.
Results

| Positive control . . . growth in 24 hours 2/2 | | |
|---|---|---|
| Organism | Carrier | Contact Time |
| Clostridium sporogenes | Sutures | 5 minutes 1/20 |

Discussion

Albeit one failure, this test once again demonstrates the significant lowering of surface tension when employing an aliphatic amine and cationic surfactant as supplements to the acid glutaraldehyde. The acid resistance test was 20 minutes.

Example III

This test was performed to determine the efficacy of the system when employing spores of Bacillus subtilis ATCC 19659, and an acid glutaraldehyde.
Results

| Positive control . . . growth in 24 hours 2/2 | | |
|---|---|---|
| Organism | Carrier | Contact Time |
| Bacillus subtilis | Sutures | 5 minutes 0/15 |

Discussion

Again the supplemented glutaraldehyde demonstrates the powerful surface active properties of aliphatic amine and cationic surfactant in aqueous solutions of glutaraldehyde. The acid resistance test was 15 minutes.

Example IV

This test was performed to determine the efficacy of vacuum on the system, employing an unsupplemented 2% acid glutaraldehyde (Uricide®).
Results

| Positive control . . . growth in 24 hours 2/2 | | | | | | |
|---|---|---|---|---|---|---|
| Organism | Carrier | Contact Time | | | | |
| Clostridium sporogenes | Sutures | 5 min 3/3 | 10 3/3 | 15 3/3 | 20 3/3 | 25 0/3 |

When Banicide® was used, the spores were inactivated within 20 minutes.
Discussion The effect of vacuum in this system is highly effective in reducing contact time when highly resistant spores are exposed to glutaraldehyde. The use of vacuum employing a supplemented 2% acid glutaraldehyde did not reduce contact time from 5–10 minutes as in Examples I–III. This further attests to the efficacy of the anionic and cationic to significantly lower surface tension.

Example V

This in-use test was performed to determine the efficacy of a supplemented acid glutaraldehyde (cationic surfactant) enhanced with vacuum and ultrasonic in inactivating handpieces (contra-angle) contaminated with Clostridium sporogenes.
Results

| Positive control . . . growth in 24 hours 2/2 | | |
|---|---|---|
| Organism | Carrier | Contact Time |
| Clostridium sporogenes | Sutures | 10 minutes 0/4 |

Discussion

This test was highly significant in that the handpiece with its gross irregular surfaces and internal cavities represent one of the most difficult instruments to sterilize. It is more difficult to sterilize than the medical endoscope, which other than ethylene oxide sterilization, must be content with disinfection in aqueous solutions of glutaraldehyde. The acid resistance test was 10 minutes.

Example VI

This test was performed to determine the efficacy of an antiseptic to inactivate highly resistant spores when supplemented with an aliphatic amine and cationic surfactant. The antiseptic employed was Betadine® (povidone-iodine).
Results

| Positive control . . . growth in 24 hours 2/2 | | | | |
|---|---|---|---|---|
| Organism | Carrier | Contact Time | | |
| Bacillus subtilis | Sutures | 2 hrs 12/12 | 2-1/2 8/8 | 3 0/8 |

Discussion

Germicides which can be applied to animate surfaces and objects are extremely important in preventing and controlling infections. The unsupplemented Betadine® requires 26 hours to inactivate the above spore employing the conventional immersion system. Any antiseptic so supplemented to enhance its sporicidal properties is extremely important in treating wound sites and other areas of the body. This enhanced activity, when exposed to this system, has been observed in hydrogen peroxide (3%), and in isopropyl alcohol (70%). The acid resistance test was 15 minutes.

Example VII

Soft contact lenses were contaminated with *Aspergillus fumigatus* exposed to hydrogen peroxide (3%). The lenses were tested to determine the contact time required to inactivate this organism on the contact lenses when a supplemented hydrogen peroxide (3%) solution was employed.
Materials 1. Contact lenses—Softmate II (Barnes Hind, Inc.,)
2. Hydrogen peroxide (3%) (Parke Davis)
3. *Aspergillus fumigatus* ATCC 16903
4. Catalase Results

| Positive control . . . growth within 24 hours 2/2 | | |
|---|---|---|
| Organism | Carrier | Contact Time |
| Aspergillus fumigatus | Contact Lenses | 5 mins 0/5 (after 7 days) |

Discussion

The ability of 3% hydrogen peroxide supplemented with cationic surfactant to inhibit this fungus within 5 minutes is significant; however, it is felt by the inventor that this contact time can be further reduced to inhibit *Aspergillus fumigatus*. The latter requires 45 minutes or more for inactivation with hydrogen peroxide 3% in the regular immersion system.

Example VIII

The purpose of this test was to determine the minimum exposure conditions required for the test system to inactivate *Bacillus subtilis* ATCC 19659 with an unsupplemented alkaline 3.2% glutaraldehyde within the closed system device. The sporicidal activity exhibited was enhanced by the vapor emitted from the 3.2% alkaline glutaraldehyde and trapped within the closed-system device.
Results

| Positive control . . . growth within 24 hours 2/2 | | |
|---|---|---|
| Organism | Carrier | Contact Time |
| Bacillus subtilis | Cylinders | 10 mins 0/10    15 mins 0/10 |

Discussion

This test was significant in that the 20 contaminated cylinders employed were negative after contact periods of 10 mins and 15 mins. at 20° C. (instead of 25° C.). It demonstrates the value of the closed system synergistically utilizing the glutaraldehyde solution and its emitted vapors. In the regular immersion system, this organism requires about 3 hours at room temperature for inactivation by 3.2% alkaline glutaraldehyde. This acid resistance test was 3 minutes.

Example IX

The purpose of this test was to determine the minimum exposure condition required for the test system to inactivate *Clostridium sporogenes*, employing a 2% alkaline glutaraldehyde.
Results

| Positive control . . . growth in 24 hours 2/2 | | |
|---|---|---|
| Organism | Carrier | Contact Time |
| Clostridium sporogenes | Sutures | 10 mins 7/96 |

Discussion

This test was significant in that the pleasing results observed with the use of an acid glutaraldehyde was shown to be just as effective when using an alkaline glutaraldehyde. This demonstrates the efficacy of the system to handle various forms of glutaraldehyde and other germicides. The acid resistance test was 20 minutes.

It will be obvious to those skilled in the art that various changes may be made without departing from the spirit of the invention, and therefore the invention is not limited to what is shown in the drawings and described in the specifications but only as indicated in the appended claims.

References

*Nonwoven Handbook.* Association of the Nonwoven Fabrics Industry.
*Surfactants And Interfacial Phenomena.* 2nd Edition. Milton J. Rosen. pp 75–80; pp. 240–252.
*Antiseptics, Disinfectants, Fungicides And Sterilization.* 2nd Edition. G. F. Reddish. pp. 203–267; pp. 330–331.

I claim:

1. A rapid sporicidal composition comprising a germicide and a cationic surfactant which is an ethoxylated aliphatic amine selected from the group consisting of bis (2-hydroxyethyl) cocoamine, polyoxyethylene (5) cocoamine, polyoxyethylene (10) cocoamine, and polyoxyethylene (15) cocoamine.

2. A rapid sporicidal composition according to claim 1 wherein the ethoxylated aliphatic amine is selected from the group consisting of bis (2-hydroxyethyl) cocoamine and polyoxyethylene (5) cocoamine.

3. A rapid sporicidal composition according to claim 1 wherein the ethoxylated aliphatic amine is selected from the group consisting of polyoxy-ethylene (10) cocoamine, and polyoxyethylene (15) cocoamine.

4. A rapid sporicidal composition according to claim 1 wherein the composition includes about 0.01 to 2% by weight of said cationic surfactant.

5. A rapid sporicidal composition according to claim 1 including a nonionic surfactant.

6. A rapid sporicidal composition according to claim 1 wherein the germicide is selected from the group consisting of quaternary ammonium salts, phenolic compounds, hydrogen peroxide, chlorine compounds, iodophors, glutaraldehyde, alcohol compounds, antibiotics, tricloson, anti-plaque agents, and persalt compounds.

7. A rapid sporicidal composition according to claim 1 wherein the germicide is glutaraldehyde comprising a saturated dialdehyde having from 2–6 carbon atoms.

8. A rapid sporicidal composition according to claim 1 wherein the composition contains about 0.1 to 2.5% by weight of said glutaraldehyde, and 0.01 to 2% by weight of cationic surfactants, selected from the group consisting of a bis (2-hydroxyethyl) cocoamine and a polyoxyethylene (5) cocoamine.

9. A rapid sporicidal composition according to claim 1 wherein the composition contains about 0.1 to 2.5% by weight of said glutaraldehyde, and 0.01 to 2% by weight of a cationic surfactant selected from the group consisting of polyoxyethylene (10) cocoamine, polyoxyethylene (15) cocoamine and a mixture thereof.

10. A rapid sporicidal composition according to claim 1 wherein there is a sufficient quantity of a lower alkanol to make a final alcoholic concentration from about 60 to 70%.

11. A rapid sporicidal composition according to claim 1 containing from about 0.01 to 2.5% by weight of a glutaraldehyde which is the germicide, about 0.01 to 2% by weight of said cationic surfactant, and an alkanol salt providing a ph of about 7–8.

12. A rapid sporicidal composition according to claim 1 containing from about 0.1 to 2.5% by weight of glutaraldehyde which is the germicide, about 0.01 to 2% by weight of said cationic surfactant, said composition having a ph of about 1–7.

13. A sterilization device comprising an envelope which is substantially impervious to liquid and gas, said device having an inner chamber provided with a hermetically sealable opening, and contains the rapid sporicidal composition of claim 1.

14. A sterilization device according to claim 13, wherein the device is provided with means to create subatmospheric pressure within the inner chamber.

15. A sterilization device according to claim 14, wherein the said device is provided with means for introducing the rapid sporicidal composition of claim 1 into the vacuumized and hermetically sealed inner chamber.

16. A sterilization device according to claim 15, wherein the means for vacuumizing the inner chamber and then introducing the composition of claim 1 into said chamber are located outside the inner chamber.

17. A sterilization device according to claim 13, including means for vacuumizing the inner chamber, and means for introducing the composition of claim 1 into the vacuumized sterilization device.

18. A sterilization device according to claim 13, wherein there are two openings for introducing contaminated objects into the inner chamber, said openings being directly opposite to each other, permitting two or more unconnected connectible components of a contaminated object to be inserted into the inner chamber through opposed openings and then connected together in said inner chamber to reassemble said object.

19. A sterilization device according to claim 13, wherein the inner chamber contains an absorbent material, the latter having absorbed therein the rapid sporicidal composition of claim 1.

20. A sterilization device of claim 13, wherein the inner chamber contains an absorbent material which carries the cationic surfactant and the germicide which, when exposed to a liquid, are released into solution forming the rapid sporicidal solution of claim 1.

21. A sterilization device according to claim 13, wherein the inner chamber contains an absorbent nonwoven fabric which carries in a dry state the rapid sporicidal composition of claim 1, which becomes activated when exposed to a liquid.

22. A sterilization device according to claim 13, including means for achieving vacuum and introducing the composition of claim 1 into the inner chamber components of said device.

23. A method of sterilizing an object by exposing the object to the composition of claim 1 for a period of time sufficient to achieve sterilization.

24. A method according to claim 23, including the preliminary steps of providing an envelope which is substantially impervious to gas and liquid, said envelope containing a member which includes a cationic surfactant, and introducing into said envelope a germicidal solution.

25. A method according to claim 24, wherein said member is an absorbent liner located within said envelope.

26. A method according to claim 23, including the step of first removing air from said envelope, and then introducing the composition of claim 1.

27. A method according to claim 23, including the step of providing a vacuum within said envelope.

28. A method according to claim 23, including the step of subjecting the object to ultrasonic waves.

29. A method of sterilizing an object, comprising the steps of providing a chamber which is substantially impervious to gas and liquid, placing a contaminated object in the chamber, removing air from said chamber and, after air is removed, introducing a sporicidal composition into the chamber to achieve sterilization thereof said sporicidal composition comprising a germicide and a cationic surfactant which is an ethoxylated aliphatic amine selected from the group consisting of bis (2-hydroxyethyl) cocoamine, polyoxyethylene (5) cocoamine, polyoxyethylene (10) cocoamine, and polyoxyethylene (15) cocoamine.

* * * * *